(12) United States Patent
Niitsu et al.

(10) Patent No.: US 10,093,931 B2
(45) Date of Patent: Oct. 9, 2018

(54) APOPTOSIS INDUCER

(71) Applicant: NITTO DENKO CORPORATION, Ibaraki-shi, Osaka (JP)

(72) Inventors: Yoshiro Niitsu, Sapporo (JP); Hiroyuki Tanaka, Ibaraki (JP)

(73) Assignee: Nitto Denko Corporation, Osaka (JP)

( * ) Notice: Subject to any disclaimer, the term of this patent is extended or adjusted under 35 U.S.C. 154(b) by 0 days.

(21) Appl. No.: 15/319,582

(22) PCT Filed: Jun. 16, 2015

(86) PCT No.: PCT/JP2015/067240
§ 371 (c)(1),
(2) Date: Dec. 16, 2016

(87) PCT Pub. No.: WO2015/194522
PCT Pub. Date: Dec. 23, 2015

(65) Prior Publication Data
US 2017/0137825 A1    May 18, 2017

(30) Foreign Application Priority Data

Jun. 17, 2014  (JP) ................. 2014-124782

(51) Int. Cl.
    *C07H 21/02*    (2006.01)
    *A61K 48/00*    (2006.01)
    (Continued)

(52) U.S. Cl.
    CPC ........ *C12N 15/1137* (2013.01); *A61K 31/713* (2013.01); *C12N 15/113* (2013.01); *C12N 2310/14* (2013.01); *C12N 2320/31* (2013.01)

(58) Field of Classification Search
    USPC ............................................ 514/44; 536/24.5
    See application file for complete search history.

(56) References Cited

U.S. PATENT DOCUMENTS

| 6,627,732 B1 | 9/2003 | Sakon et al. |
| 2004/0018985 A1 | 1/2004 | Sakon et al. |

(Continued)

FOREIGN PATENT DOCUMENTS

| CN | 1953762 A | 4/2007 |
| EP | 2 724 729 A1 | 4/2014 |

(Continued)

OTHER PUBLICATIONS

Bae et al., Suppression of Autophagy by FIP200 Deletion Impairs DNA Damage Repair and Increases Cell Death upon Treatments with Anticancer Agents, Molecular Cancer Research, 2011, 9(9), p. 1232-1241.

(Continued)

*Primary Examiner* — Terra C Gibbs
(74) *Attorney, Agent, or Firm* — Knobbe, Martens, Olson & Bear, LLP

(57) ABSTRACT

The purpose of the present invention is to provide: a composition for effectively inducing apoptosis and/or proliferation inhibition in cells; and a method in which the composition is used. The present invention relates to: an agent for inducing apoptosis, which contains a GST-π-inhibiting drug and a RB1CC1-inhibiting drug as active ingredients; a pharmaceutical composition which contains the agent; a method for treating a disease associated with an abnormality in apoptosis, in which the agent is used; and others.

2 Claims, 4 Drawing Sheets
Specification includes a Sequence Listing.

(51) Int. Cl.
*A61K 31/713* (2006.01)
*C12N 15/11* (2006.01)
*C12N 15/113* (2010.01)

(56) References Cited

U.S. PATENT DOCUMENTS

| | | |
|---|---|---|
| 2004/0029275 A1 | 2/2004 | Brown et al. |
| 2004/0037833 A1 | 2/2004 | Mather et al. |
| 2004/0171814 A1 | 9/2004 | Mather et al. |
| 2005/0004064 A1 | 1/2005 | Tei et al. |
| 2005/0152907 A1 | 7/2005 | Liang et al. |
| 2008/0207553 A1 | 8/2008 | Zhao et al. |
| 2008/0312174 A1 | 12/2008 | Yu et al. |
| 2010/0144659 A1 | 6/2010 | Niitsu et al. |
| 2013/0064815 A1 | 3/2013 | Coller |
| 2014/0315975 A1 | 10/2014 | Niitsu et al. |

FOREIGN PATENT DOCUMENTS

| | | | |
|---|---|---|---|
| JP | 2003-219893 A | | 8/2003 |
| JP | 2005-532050 A | | 10/2005 |
| JP | 2006-506071 A | | 2/2006 |
| JP | 2007-529197 A | | 10/2007 |
| JP | WO 2012/176282 A1 | * | 12/2012 |
| WO | WO 1995/08563 A1 | | 3/1995 |
| WO | WO 1996/40205 A1 | | 12/1996 |
| WO | WO 1999/54346 A1 | | 10/1999 |
| WO | WO 2004/001381 | | 12/2003 |
| WO | WO 2004/043239 | | 5/2004 |
| WO | WO 2005/028498 | | 3/2005 |
| WO | WO 2005/112973 A1 | | 12/2005 |
| WO | WO 2006/078774 | | 7/2006 |
| WO | WO 2008/120815 A1 | | 10/2008 |
| WO | WO 2009/036368 A2 | | 3/2009 |
| WO | WO 2010/014117 A1 | | 2/2010 |
| WO | WO 2012/170952 A2 | | 12/2012 |
| WO | WO 2012/176282 A1 | | 12/2012 |

OTHER PUBLICATIONS

Ban et al., Transfection of Glutathione S-Transferase (GST)-π Antisense Complementary DNA Increases the Sensitivity of a Colon Cancer Cell Line to Adriamycin, Cisplatin, Melphalan, and Etoposide, Cancer Research, 1996;56(15):3577-82.

Bos, ras Oncogenes in Human Cancer: A Review, Cancer Research, 1989;49(17):4682-9.

Chano et al., Identification of RB1CC1, a novel gene that can induce RB1 in various human cells, Oncogene. 2002;21(8):1295-8.

Chano et al., RB1CC1 insufficiency causes neuronal atrophy through mTOR signaling alteration and involved in the pathology of Alzheimer's diseases, Brain Res., 2007, 1168, p. 97-105.

Futreal et al., Nat Rev Cancer, A Census of Human Cancer Genes, 2004;4(3):177-183, p. 1-16.

Hall et al., Possible Role of Inhibition of Glutathione S-Transferase in the Partial Reversal of Chlorambucil Resistance by Indomethacin in a Chinese Hamster Ovary Cell Line, Cancer Research. 1989;49(22):6265-6268.

Hokaiwado et al., Glutathione S-transferase Pi mediates proliferation of androgen-independent prostate cancer cells, Carcinogenesis. 2008;29(6):1134-1138.

Ikeda et al., Inhibition of Autophagy Enhances Sunitinib-Induced Cytotoxicity in Rat Pheochromocytoma PC12 cells, Journal Pharmacological Sciences, 2013, 121(1), p. 67-73.

Klionsky et al., A Unified Nomenclature for Yeast Autophagy-Related Genes, Developmental Cell. 2003;5(4):539-545.

Levi et al., Multiple K-ras Codon 12 Mutations in Cholangiocarcinomas Demonstrated with a Sensitive Polymerase Chain Reaction Technique, Cancer Research, 1991;51(13):3497-3502.

Li et al., FIP200 is Involved in Murine Pseudomonas Infection by Regulating HMGB1 Intracellular Translocation, Cell Physiol. Biochem., 2014.5, 33(6), p. 1733-1744.

Marcucci F. et al., Active targeting with particulate drug carriers in tumor therapy: fundamentals and recent progress, Drug Discovery Today. 2004;9(5):219-228.

Nakajima et al., Reversal of Multiple Drug Resistance in Cholangiocarcinoma by the Glutathione S-Transferase-π-Specific Inhibitor $O^1$-Hexadecyl-*-glutamyl-S benzylcysteinyl-D-phenylglycine Ethylester, The Journal of Pharmacology and Experimental Therapeutics, 2003;306(3):861-869.

Nishimura et al., RB1CC1 Protein Suppresses Type II Collagen Syntheis in Chondrocytes and Causes Dwarfism, the Journal Biological Chemistry, 2011, 286(51), p. 43925-43932.

Nishita et al., Abstract No. 1065: Regulation of autophagy and MAPK signaling by glutathione S-transferase-TT in KRAS mutated cancer cells, Cancer Research AACR Journals 102nd Annual Meeting, 2011;71, 1 page.

Nobs et al., Current Methods for Attaching Targeting Ligands to Liposomes and Nanoparticles, Journal of Pharmaceutical Sciences, 2004;93(8):1980-1992.

Park et al., Properties of circular dumbbell RNA/DNA chimeric oligonucleotides containing antisense phosphodiester oligonucleotides, Nucleic Acids Symposium Series 1999;(42):225-226.

Pirollo et al., Targeted Delivery of Small Interfering RNA: Approaching Effective Cancer Therapies, Cancer Research 2008;68(5):1247-1250.

Ruoslahti et al., Targeting of drugs and nanoparticles to tumors, The Journal of Cell Biology, 2010;188(6):759-768.

Takahashi et al., Glutathione S transferases-π, Gan To Kagaku Ryoho. 1994;21(7):945-51.

Tew et al., Ethacrynic Acid and Piriprost as Enhancers of Cytotoxicity in Drug Resistant and Sensitive Cell Lines, Cancer Research, 1988;48(13):3622-3625.

Torchilin, Targeted Pharmaceutical Nanocarriers for Cancer Therapy and Imaging, The AAPS Journal 2007;9(2):E128-147.

Torchilin, Recent Advances With Liposomes as Pharmaceutical Carriers, Natural Reviews Drug Discovery, 2005;4(2):145-160.

Wei et al., p62/SQSTM1 synergizes with autophagy for tumor growth in vivo, Genes Development, 2014, 28(11), p. 1204-1216.

Yang et al., Mammalian autophagy: core molecular machinery and signaling regulation, Current Opinion in Cell Biology 2010;22(2):124-131.

Yao et al., Deletion of autophagy inducer RB1CC1 results in degeneration of the retinal pigment epithelium, Autophagy, 2015, 11(6), p. 939-953.

Amaravadi et al., "Autophagy inhibition enhances therapy-induced apoptosis in a Myc-induced model of lymphoma" *J. Clin. Invest.* (2007) 117:326-336.

Eickelmann et al., Expression of NAD(P)H: quinone oxidoreductase and glutathisone S-transferases alpha and pi in human renal cell carcinoma and in kidney cancer-derived cell lines', Carcinogenesis, Feb. 1994; 15(2): 219-25.

Fesik et al., Promotion Apoptosis as a Strategy for Cancer Drug Discovery, Nature Reviews, vol. 5, Nov. 2005, p. 876-885.

Gao et al., "Autophagy negatively regulates Wnt signaling by promoting Dishevelled degradation" Nature Cell Biology (2010) 12(8):781-790 with Supplementary Information 1-8.

Gedaly et al., PI-103 and Sorafenib Inhibit Hepatocellular Carcinoma Cell Proliferation by Blocking Ras/Raf/MAPK and PI3K/AKT/mTOR Pathways, Anticancer Research (2010) 30:4951-4958.

Ito et al Igaku Shoin's Medical Dictionary Mar. 2003, 1$^{st}$ Edition, 654-655.

Katopodis et al., "MG-63 Osteoblast-like Cells Enhance the Osteoprotegerin Expression of PC-3 Prostate Cancer Cells." Anticancer Research, 2009, pp. 4013-4018, vol. 29.

Kim et al., "Anti-tumor Activity of the Ginsenoside Rk1 in Human Hepatocellular Carcinoma Cells through Inhibition of Telomerase Activity and Induction of Apoptosis", Biol. Pharm. Bull. 31(5) 826-830, vol. 31, No. 5 (2008).

Ko et al., Autophagy Inhibition Enhances Apotosis Induced by Ginsenoside Rk1 in Hepatocellular Carcinoma Cells, *Biosci. Biotechnol. Biochem.* (2009) 73(10):2183-2189.

Kondo et al., Autophagy in Cancer, Ishiyaku Publishers, Inc., Feb. 18, 2006, vol. 216, No. 7, 525-529.

(56) References Cited

OTHER PUBLICATIONS

Kondo et al., The Role of Autophagy in Cancer Development and Response to Therapy, Nature Reviews, vol. 5, Sep. 2005, p. 726-734.
Kozlowski, et al. "Metastatic Behavior of Human Tumor Cell Lines Grown in the Nude Mouse." Cancer Research, 1984, pp. 3522-3529, vol. 44.
Lee, et al., Roles of AKT1 and AKT2 in non-small cell lung cancer cell survival, growth, and migration, Cancer Science, Oct. 2011, vol. 102, No. 10, p. 1822-1828.
Li, et al., Autophagy protects LNCaP Cells under androgen deprivation conditions, Autophagy 4:1, 54-60, Jan. 1, 2008.
Maiuri et al., Control of autophagy by oncogenes and tumor suppressor genes, Cell Death and Differentiation (2009) 16, 87-93.
Miyanishi et al., "Glutathione S-Transferase-π Overexpression is Closely Associated with K-ras Mutation During Human Colon Carcinogenesis" *Gastroenterology* ( 2001) 121(4):865-874.
Miyazawa et. al., "Induction of autophagy and apoptosis in leukemia cells by vitamin K2" vol. 48, No. 9, 2007, p. 1097, Dai 69 Kai The Japanese Society of Hematology, Dai 49 Kai The Japanese Society of Clinical Hematology Godo Sokai Program Shorokushu.
Mochizuki et al., Inhibition of NADPH oxidase 4 activates apoptosis via the AKT/apoptosis signal-regulating kinase 1 pathway in pancreatic cancer PANC-1 cells, Oncogene (2006)25, 3699-3707.
Nagaprashantha et al., "2'-Hydroxyflavanone inhibits proliferation, tumor vascularization and promotes normal differentiation in VHL-mutant renal cell carcinoma" Carcinogenesis (2011) 32(4):568-575.
Nishita, Hiroki et al, "GSTP1 enhances Raf-1/MEK/ERK pathway by preventing proteasomal degradation of Raf-1 in human colon cancer cells", Report of the 69th Annual Meeting of the Japanese Cancer Association (Aug. 23, 2010) p. 211.
Nobouka et al, "Glutathione-S-Transferase P1-1 Protects Aberrant Crypt Foci From Apoptosis Induced by Deoxycholic Acid" Gastroenerology 127:428-433 2004.
PAL, Akt inhibitors in clinical development for the treatment of cancer, Expert Opinion on Investigation Drugs, vol. 19, No. 11, Nov. 1, 2010, pp. 1355-1366.
Payne et al, "Deoxycholate, an Endogenous Cytotoxin/Genotoxin, Induces the Authophagic Stress-Survival Pathway: Implications for Colon Carcinogensis" Journal of Toxicology vol. 2009, Article 785907, 14 pages, 2009.
Scharmach et al. "Glutathione S-transferase expression and isoenzyme composition during cell differentiation of Caco-2 cells", Toxicology. Nov. 30, 2009;265(3):122-26. doi: 10.1016/j.tox.2009.09.017. Epub Oct. 1, 2009.
Sun et al. "Bioluminescent imaging study; Fak inhibitor, PF-562,271, preclinical study in PC3M-luc-C6 local implant and metastasis xenograft models." Cancer Biology and Therapy, 2010, pp. 1-6, vol. 10:1.
Swami "Akt: a double-edged sword" Nature Reviews Cancer published online Dec. 29, 2008, pp. 76-77.
Takanashi et al., The role of GSTpi as a mediator of Map kinase in colon carcinogenesis, Proceeding of the Japanese Cancer Association, 2007 vol. 66, p. 181.
Takayama et al "Chemoprevention of colorectal cancer targeting GST-pi" Frontiers in Gastroenterology, Jan. 2010, vol. 15, No. 1, p. 11-17.
Thimmaiah, et al., Identification of $N^{10}$-Substituted Phenoxazines as Potent and Specific Inhibitors of Akt Signaling, The Journal of Biological Chemistry, Sep. 9, 2005, vol. 280, No. 36, p. 31924-31935.
Tsukamoto et. al., "Tenkai Suru Proteasome Sogaizai Kenkyu", Experimental Medicine, 2008, vol. 26, No. 2, pp. 242 to 247.
Uchida, et al., MiR-133a induces apoptosis through direct regulation of GSTP1 in bladder cancer cell lines, Urologic Oncology. [online], Mar. 10, 2011, vol. 31, Issue 1, p. 115-123, internet <DOI:10.1016/j.urolonc.2010.09.017>.
Wee et al. "P13K Pathway Activation Mediates Resistance to MEK Inhibitors in KRAS Mutant Cancers." Cancer Research, 2009, pp. 4286-4293, vol. 69.
Yoo et al., "Oncogenic ras-induced Down-regulation of Autophagy Mediator Beclin-1 is Required for Malignant Transformation of Intestinal Epithelial Cells," The Journal of Biological Chemistry, vol. 285, No. 8, pp. 5438-5449, Feb. 19, 2010.
Database Accession No. NLM22568098, US National Library of Medicine (2012), Medline Database XP002778219.
Extended European Search Report dated Mar. 2, 2018 for EP Application No. 15810564.3.
Anti-RB1CC1 Product Datasheet, Atlas Antibodies, dated Dec. 2012.

\* cited by examiner

[FIG. 1]
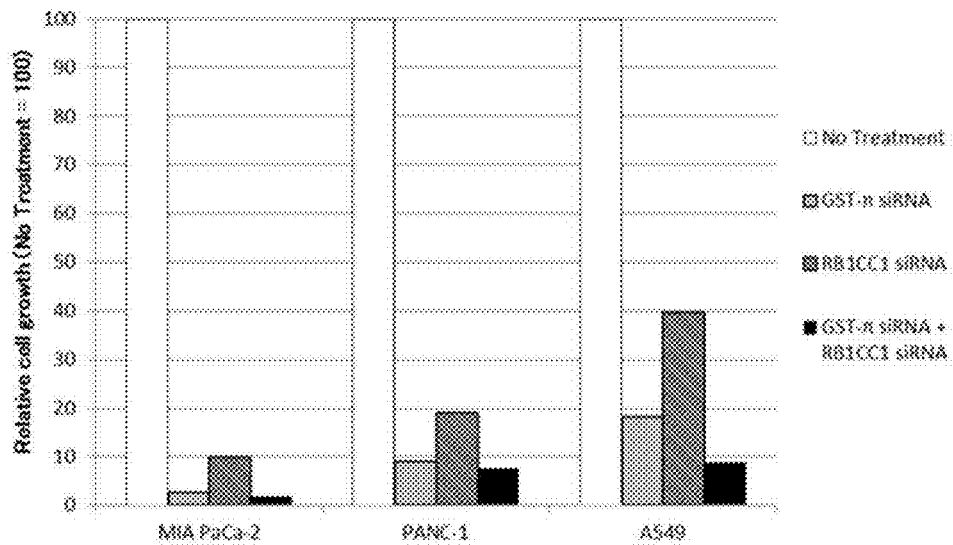
[FIG. 2]
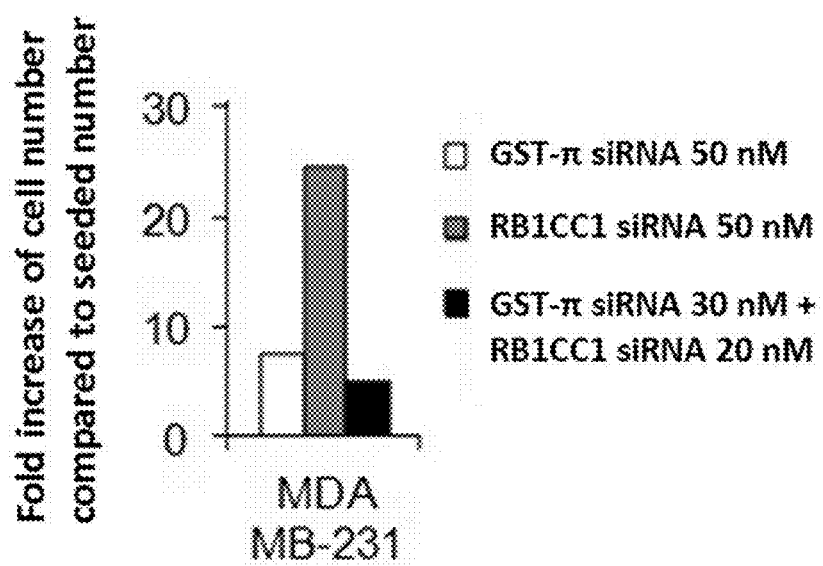

[FIG. 3]
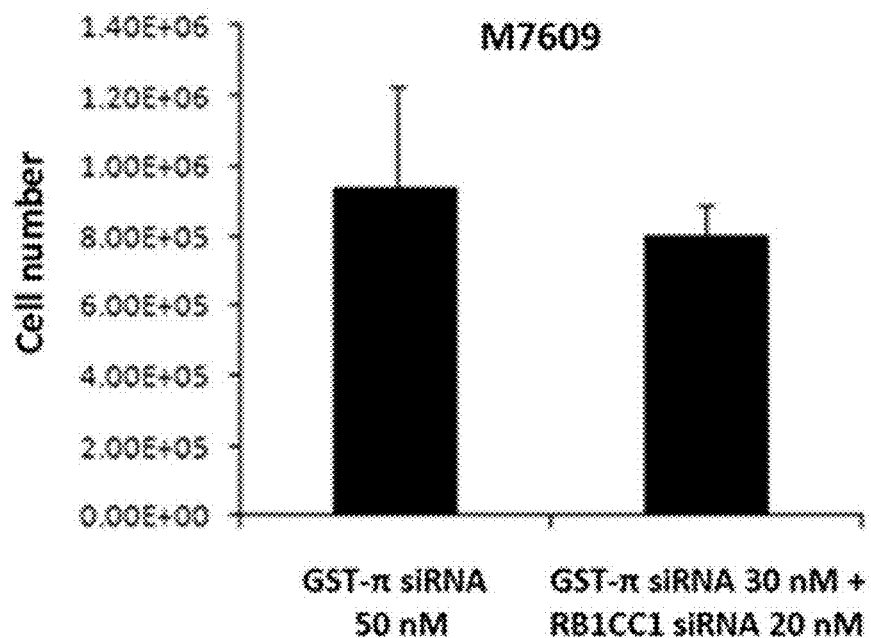
[FIG. 4]
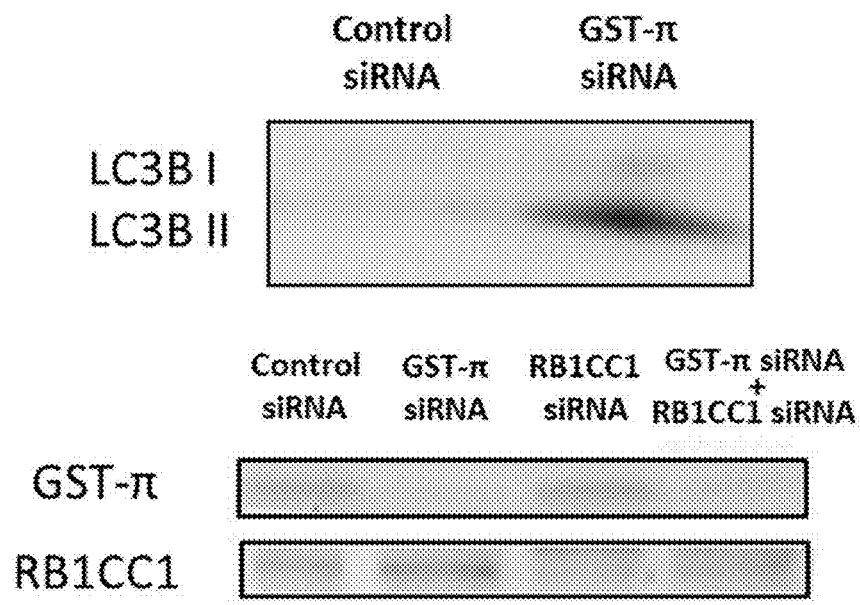

[FIG. 5]
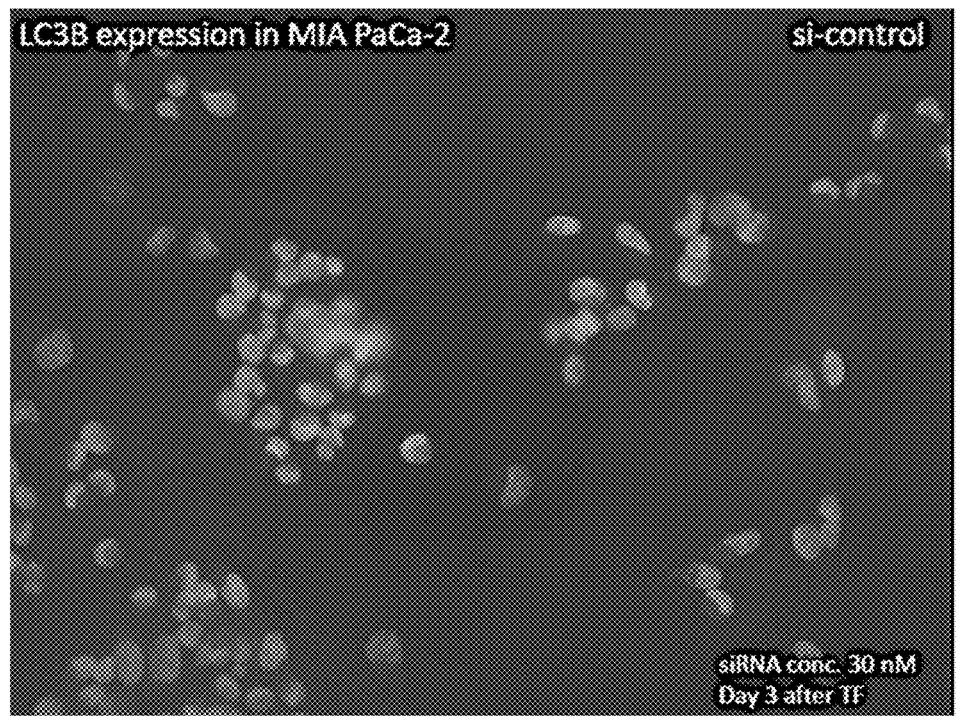
[FIG. 6]

[FIG. 7]
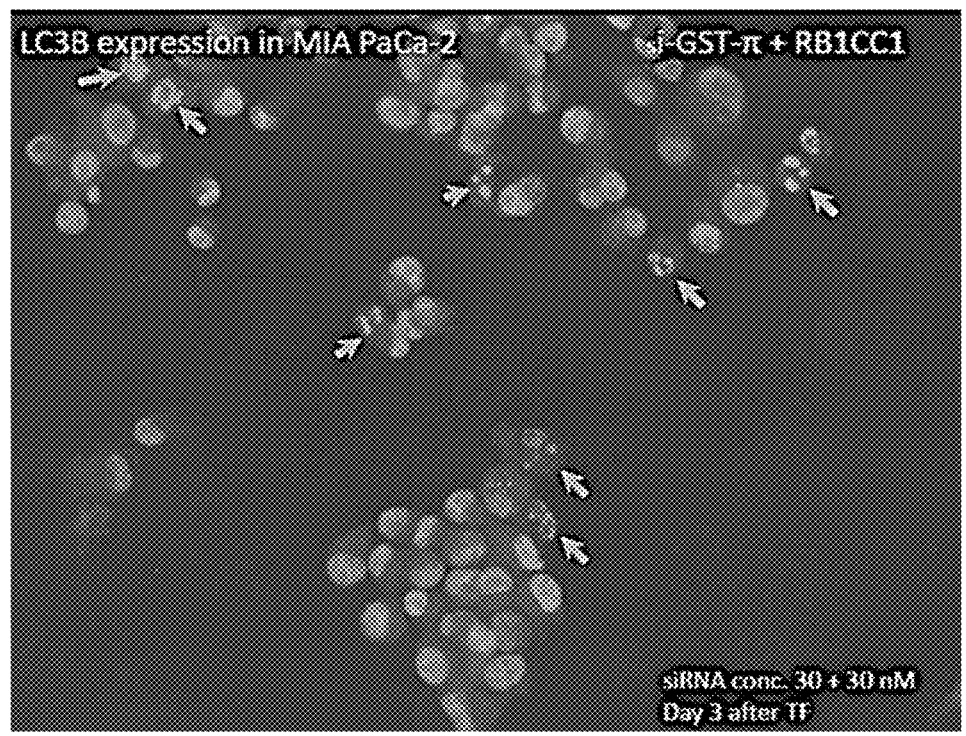
[FIG. 8]
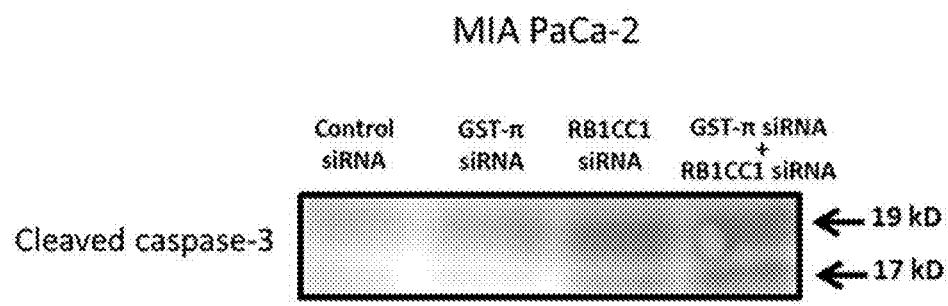

SEQUENCE LISTING

<160> NUMBER OF SEQ ID NOS: 6

<210> SEQ ID NO 1
<211> LENGTH: 21
<212> TYPE: DNA
<213> ORGANISM: Artificial Sequence
<220> FEATURE:
<223> OTHER INFORMATION: Description of Combined DNA/RNA Molecule: GST-
      pi siRNA sense strand

<400> SEQUENCE: 1
gggaggcaag accuucauut t                                              21

<210> SEQ ID NO 2
<211> LENGTH: 21
<212> TYPE: DNA
<213> ORGANISM: Artificial Sequence
<220> FEATURE:
<223> OTHER INFORMATION: Description of Combined DNA/RNA Molecule: GST-
      pi siRNA antisense strand

<400> SEQUENCE: 2
aaugaagguc uugccuccct g                                              21

<210> SEQ ID NO 3
<211> LENGTH: 21
<212> TYPE: DNA
<213> ORGANISM: Artificial Sequence
<220> FEATURE:
<223> OTHER INFORMATION: Description of Combined DNA/RNA Molecule:
      RB1CC1 siRNA sense strand

<400> SEQUENCE: 3
gggacggaua caaauccaat t                                              21

<210> SEQ ID NO 4
<211> LENGTH: 21
<212> TYPE: DNA
<213> ORGANISM: Artificial Sequence
<220> FEATURE:
<223> OTHER INFORMATION: Description of Combined DNA/RNA Molecule:
      RB1CC1 siRNA antisense strand

<400> SEQUENCE: 4
uuggauuugu auccguccca g                                              21

<210> SEQ ID NO 5
<211> LENGTH: 21
<212> TYPE: DNA
<213> ORGANISM: Artificial Sequence
<220> FEATURE:
<223> OTHER INFORMATION: Description of Combined DNA/RNA Molecule:
      Control siRNA sense strand

<400> SEQUENCE: 5
acgugacacg uucggagaat t                                              21

<210> SEQ ID NO 6
<211> LENGTH: 21
<212> TYPE: DNA
<213> ORGANISM: Artificial Sequence
<220> FEATURE:
<223> OTHER INFORMATION: Description of Combined DNA/RNA Molecule:
      Control siRNA antisense strand

<400> SEQUENCE: 6
uucuccgaac gugucacgut t                                              21

APOPTOSIS INDUCER

TECHNICAL FIELD

The present invention relates to a novel apoptosis-inducing agent, a novel cell proliferation-suppressing agent, a novel autophagy-suppressing agent, a pharmaceutical composition containing the apoptosis-inducing agent, cell proliferation-suppressing agent, or autophagy-suppressing agent, and a novel therapeutic method for a disease associated with abnormal apoptosis, cell proliferation, or autophagy.

BACKGROUND ART

Cancer is one of the most important and troublesome diseases that confront mankind, and an enormous amount of research effort into the treatment thereof is being carried out. Cancer is a disease in which cells grow uncontrollably due to gene mutation, epigenetic abnormality, etc. With regard to genetic abnormalities in cancer, a large number have already been reported (e.g., Non-Patent Literature 1, etc.), and it is thought that many thereof are somehow associated with signal transduction related to cell proliferation, differentiation and survival. Furthermore, due to such genetic abnormalities, abnormalities occur in signal transduction in cells consisting of normal molecules, and this causes activation or inactivation of a specific signal cascade and can finally become one factor triggering abnormal cell proliferation. Early cancer treatment has focused on suppression of cell proliferation itself, but since such a treatment also suppresses proliferation of cells with physiologically normal proliferation, it was accompanied by side effects such as hair loss, gastrointestinal dysfunction, or bone marrow suppression. In order to reduce such side effects, development of drugs for the treatment of cancer based on a new concept such as molecularly targeted drugs that target cancer-specific genetic abnormalities or abnormalities in signal transduction is being undertaken.

As a cancer-specific genetic abnormality, abnormalities in KRAS (V-Ki-ras2 Kirsten rat sarcoma viral oncogene homolog) are well known. KRAS is a low molecular weight GTP-binding protein (also called a low molecular weight G protein) positioned downstream of a tyrosine kinase receptor such as EGFR (Epidermal growth factor receptor) or PDGFR (Platelet-derived growth factor receptor), and plays a part in transferring a signal related to growth or differentiation from these receptors to a downstream MAPK (Mitogen-activated protein kinase) cascade. Normal KRAS is activated via Grb2 (Growth factor receptor-bound protein 2) and SOS (Son of Sevenless) by means of tyrosine kinase activation of a receptor activated by ligand binding, and phosphorylates a MAPK such as Raf (Rapidly accelerated fibrosarcoma) so as to drive the MAPK cascade, but mutant type KRAS is constantly activated without stimulation from a receptor and continues to transmit a growth signal. It is thought that because of this, abnormal cell growth occurs.

Expression of glutathione-S-transferase (GST), which is one of the enzymes that catalyze glutathione conjugation, in particular GST-π (glutathione S-transferase pi, also called GSTP1), increases in various cancer cells, and it has been pointed out that there is a possibility that this is one factor for resistance to some anticancer agents. In fact, it is known that when GST-π antisense DNA or a GST-π inhibitor is made to act on a cancer cell line that is overexpressing GST-π and exhibiting drug resistance, the drug resistance is suppressed (Non-Patent Literatures 2 to 4). Furthermore, in a recent report, when GST-π siRNA is made to act on an androgen-independent prostate cancer cell line that is overexpressing GST-π, proliferation thereof is suppressed and apoptosis is increased (Non-Patent Literature 5). Moreover, it has been reported that, when GST-π siRNA is made to act on a cancer line that has a KRAS mutation, activation of Akt is suppressed, and autophagy increases, but there is only a medium degree of induction of apoptosis (Non-Patent Literature 6), and Patent Literature 1 describes an apoptosis-inducing agent, etc. that includes a drug that suppresses GST-π and a drug that suppresses autophagy as active ingredients.

However, there has so far been hardly any clarification of the relationship between GST-π and cell proliferation or apoptosis, the molecular mechanism of GST-π, and the role, etc., of GST-π in various types of intracellular signal transduction. Intracellular signal transduction is very complicated; one molecule may influence the effect of a plurality of molecules, or conversely one molecule may be influenced by a plurality of molecules, when the effect of a certain molecule is inhibited, another signal cascade may be activated, and an expected effect often cannot be obtained. Therefore, it is necessary to elucidate the complicated cell signal transduction mechanism in order to develop superior molecularly targeted drugs, but only a very small part of the mechanism has been elucidated in many years of research, and further research effort is needed.

CITATION LIST

Patent Literatures

[PL1] International Patent Application WO2012/176282

Non-Patent Literatures

[NPL1] Futreal et al., Nat Rev Cancer. 2004; 4 (3): 177-83
[NPL2] Takahashi and Niitsu, Gan To Kagaku Ryoho. 1994; 21 (7): 945-51
[NPL3] Ban et al., Cancer Res. 1996; 56 (15): 3577-82
[NPL4] Nakajima et al., J Pharmacol Exp Ther. 2003; 306 (3): 861-9
[NPL5] Hokaiwado et al., Carcinogenesis. 2008; 29 (6): 1134-8
[NPL6] Nishita et al., AACR 102nd Annual Meeting, Abstract No. 1065

SUMMARY OF THE INVENTION

Problems to be Solved by the Invention

It is an object of the present invention to provide a composition for inducing apoptosis and/or proliferation inhibition effectively in cells and a method using same.

Means for Solving the Problems

While carrying out intensive research in order to elucidate the molecular mechanism of GST-π, the present inventors have found that when there is simultaneous inhibition of expression of GST-π and expression of RB1CC1 (RB1-inducible coiled-coil protein 1) in cells, compared with a case in which expression of only one of the two is inhibited, cell proliferation is more strongly suppressed, and have further found that autophagy, which is induced by inhibition of expression of GST-π, is markedly suppressed by simultaneously inhibiting expression of RB1CC1, and apoptosis is strongly induced, and the present invention has thus been accomplished.

That is, the present invention relates to the following.

(1) An agent for inducing apoptosis, the agent comprising as active ingredients a drug that suppresses GST-π and a drug that suppresses RB1CC1.
(2) An agent for suppressing cell proliferation, the agent comprising as active ingredients a drug that suppresses GST-π and a drug that suppresses RB1CC1.
(3) An agent for suppressing autophagy in a cell in which GST-π is suppressed, the agent comprising as an active ingredient a drug that suppresses RB1CC1.
(4) An agent for enhancing the induction of apoptosis and/or the suppression of cell proliferation by a drug that suppresses GST-π, the agent comprising as an active ingredient a drug that suppresses RB1CC1.
(5) The agent according to any one of (1) to (4), wherein the active ingredient is selected from the group consisting of an RNAi molecule, a ribozyme, an antisense nucleic acid, a DNA/RNA chimera polynucleotide, and a vector expressing same.
(6) A pharmaceutical composition comprising the agent according to any one of (1) to (5).
(7) The pharmaceutical composition according to (6), the composition being for use in the treatment of a disease caused by abnormal cell proliferation.
(8) The pharmaceutical composition according to (6), the composition being for use in the treatment of a cancer.

Effects of the Invention

Since the apoptosis-inducing agent of the present invention can induce apoptosis and suppress cell proliferation more effectively compared with a conventional one, it is extremely useful as a pharmaceutical composition. In the treatment of cancer in particular, since cancer cells can be killed by apoptosis, not only is it possible to inhibit the progression of cancer, but an effect in making cancer regress can also be expected.

BRIEF DESCRIPTION OF DRAWINGS

FIG. 1 is a graph showing the effect of suppressing cell proliferation by knockdown of GST-π and/or RB in various cancer cells.

FIG. 2 is a graph showing the effect of suppressing cell proliferation by knockdown of GST-π and/or RB1CC1 in MDA-MB-231 cells.

FIG. 3 is a graph showing the effect of suppressing cell proliferation by knockdown of GST-π or GST-π+RB1CC1 in M7609 cells.

FIG. 4 is a diagram showing that autophagy is induced by knockdown of GST-π in MIA PaCa-2 cells.

FIG. 5 is a photographic diagram showing the result of immunostaining MIA PaCa-2 cells, treated with Control siRNA, with an anti-LC3B antibody.

FIG. 6 is a graph showing the result of immunostaining MIA PaCa-2 cells, treated with GST-π siRNA, with an anti-LC3B antibody.

FIG. 7 is a graph showing the result of immunostaining MIA PaCa-2 cells, treated with both GST-π siRNA and RB1CC1 siRNA, with an anti-LC3B antibody.

FIG. 8 is a diagram showing the result of detecting cleaved caspase-3 in MIA PaCa-2 cells treated with various types of siRNA.

MODES FOR CARRYING OUT THE INVENTION

The present invention relates to an agent or composition for suppressing cell proliferation (hereinafter, also called a "cell proliferation-suppressing agent" or "cell proliferation-suppressing composition") and an agent or composition for inducing apoptosis (hereinafter, also called an "apoptosis-inducing agent" or an "apoptosis-inducing composition") that contains as active ingredients a drug that suppresses GST-π and a drug that suppresses RB1CC1.

GST-π is an enzyme, encoded by GSTP1 gene, that catalyzes glutathione conjugation. GST-π is present in various animals, including humans, and its sequence information is known (e.g., human: NP_000843 (NM_000852), rat: NP_036709 (NM_012577), mouse: NP_038569 (NM_013541), etc. The numbers denote NCBI database accession numbers; those outside parentheses are amino acid sequence numbers, and those inside parentheses are base sequence numbers).

RB1CC1 is a protein encoded by the RB1CC1 gene and is known to induce expression of RB1 (retinoblastoma 1), which is a cancer suppressor gene (Chano et al., Oncogene. 2002; 21 (8): 1295-8). RB1CC1 is present in various animals, including humans, and its sequence information is known (e.g., human: BAB69690 (AB059622), rat: NP_001101371 (NM_001107901), mouse: NP_033956 (NM_009826), etc. The numbers denote NCBI database accession numbers; those outside parentheses are amino acid sequence numbers, and those inside parentheses are base sequence numbers).

Since there is a possibility of the occurrence of a mutation of a gene sequence or an amino acid sequence between biological individuals that does not impair the physiological function of a protein, GST-π and GSTP1 gene, and RB1CC1 and RB1CC1 gene in the present invention are not limited to proteins or nucleic acids having the same sequence as the known sequences, and can include those that have a sequence that is different from the above sequence by one or more amino acids or bases, typically one or a few, for example, one, two, three, four, five, six, seven, eight, nine, or ten amino acids or bases, but have an equivalent function to that of the known GST-π and RB1CC1. The specific functions of GST-π and RB are as described later.

In the present specification, phrases such as "when used herein", "used herein", "in the present specification", and "described herein" mean, unless otherwise specified, that the description following them applies to all of the inventions described in the present specification. Furthermore, unless otherwise defined, all of the technical terms and scientific terms used herein have the same meaning as that usually understood by a person skilled in the art. The entireties of all of the patents, patent publications, and other publications referred to herein are incorporated herein by reference.

Examples of the "drug that suppresses GST-π" used herein include, but are not limited to, a drug that suppresses GST-π production and/or activity and a drug that promotes GST-π degradation and/or inactivation. Examples of the drug that suppresses GST-π production include, but are not limited to, an inhibitory nucleic acid such as an RNAi molecule, ribozyme, antisense nucleic acid, or DNA/RNA chimera polynucleotide for DNA encoding GST-π, or a vector expressing same.

Examples of the drug that suppresses GST-π activity include, but are not limited to, a substance that binds to GST-π such as, for example, glutathione, a glutathione analog (e.g., those described in WO 95/08563, WO 96/40205, WO 99/54346, Non-Patent Literature 4, etc.), ketoprofen (Non-Patent Literature 2), indomethacin (Hall et al., Cancer Res. 1989; 49 (22): 6265-8), ethacrynic acid, Piloprost (Tew et al., Cancer Res. 1988; 48 (13): 3622-5), an anti-GST-π antibody, and a GST-π dominant negative mutant. These drugs are either commercially available or may be produced appropriately based on known techniques.

The drug that suppresses GST-π production or activity is preferably an inhibitory nucleic acid such as an RNAi molecule, ribozyme, antisense nucleic acid, or DNA/RNA chimera polynucleotide for DNA encoding GST-π, or a vector expressing same, in terms of high specificity and a low possibility of side effects.

Suppression of GST-π may be determined by the expression or activity of GST-π in cells being suppressed compared with a case in which a GST-π suppressing agent is not utilized. Expression of GST-π may be evaluated by any known technique; examples thereof include, but are not limited to, an immunoprecipitation method utilizing an anti-GST-π antibody, EIA (enzyme immunoassay) (e.g., ELISA (enzyme-linked immunosorbent assay), etc.), RIA (radioimmunoassay) (e.g., IRMA (immunoradiometric assay), RAST (radioallergosorbent test), RIST (radioimmunosorbent test), etc.), a western blot method, an immunohistochemical method, an immunocytochemical method, a flow cytometry method, various hybridization methods utilizing a nucleic acid that specifically hybridizes with a nucleic acid encoding GST-π or a unique fragment thereof, or a transcription product (e.g., mRNA) or splicing product of said nucleic acid, a northern blot method, a Southern blot method, and various PCR methods.

Furthermore, the activity of GST-π may be evaluated by analyzing a known activity of GST-π including, but not limited to, binding to a protein such as, for example, Raf-1 (in particular phosphorylated Raf-1) or EGFR (in particular phosphorylated EGFR) by means of any known method such as for example an immunoprecipitation method, a western blot method, a mass analysis method, a pull-down method or a surface plasmon resonance (SPR) method.

Examples of the "drug that suppresses RB1CC1" used herein include, but are not limited to, a drug that suppresses RB1CC1 production and/or activity and a drug that promotes RB1CC1 degradation and/or inactivation. Examples of the drug that suppresses RB1CC1 production include, but are not limited to, an inhibitory nucleic acid such as an RNAi molecule, ribozyme, antisense nucleic acid, or DNA/RNA chimera polynucleotide for DNA encoding RB1CC1, or a vector expressing same.

Examples of the drug that suppresses RB1CC1 activity include, but are not limited to, an anti-RB1CC1 antibody and an RB1CC1 dominant negative mutant. These drugs are either commercially available or may be produced appropriately based on known techniques.

The drug that suppresses RB1CC1 production or activity is preferably an inhibitory nucleic acid such as an RNAi molecule, ribozyme, antisense nucleic acid, or DNA/RNA chimera polynucleotide for DNA encoding RB1CC1 or a vector expressing same, in terms of high specificity and a low possibility of side effects.

Suppression of RB1CC1 may be determined by the expression or activity of RB1CC1 in cells being suppressed compared with a case in which an RB1CC1-suppressing agent is not utilized. Expression of RB1CC1 may be evaluated by any known technique; examples thereof include, but are not limited to, an immunoprecipitation method utilizing an anti-RB1CC1 antibody, EIA (e.g., ELISA, etc.), RIA (e.g., IRMA, RAST, RIST, etc.), a western blot method, an immunohistochemical method, an immunocytochemical method, a flow cytometry method, various hybridization methods utilizing a nucleic acid that specifically hybridizes with a nucleic acid encoding RB or a unique fragment thereof, or a transcription product (e.g., mRNA) or splicing product of said nucleic acid, a northern blot method, a Southern blot method and various PCR methods.

Furthermore, the activity of RB1CC1 may be evaluated by analyzing a known activity of RB1CC1 including, but not limited to, for example an activity of inducing RB1, by any known technique; examples thereof include an immunoprecipitation method utilizing an anti-RB1CC1 antibody, EIA (e.g., ELISA, etc.), RIA (e.g., IRMA, RAST, RIST, etc.), a western blot method, an immunohistochemical method, an immunocytochemical method, a flow cytometry method, various hybridization methods utilizing a nucleic acid that specifically hybridizes with a nucleic acid encoding RB1 or a unique fragment thereof, or a transcription product (e.g., mRNA) or splicing product of said nucleic acid, a northern blot method, a Southern blot method and various PCR methods.

When used herein, the RNAi molecule denotes any molecule that causes RNA interference, including, but not limited to, a nucleic acid molecule such as siRNA (small interfering RNA), miRNA (micro RNA), shRNA (short hairpin RNA), ddRNA (DNA-directed RNA), piRNA (Piwi-interacting RNA) or rasiRNA (repeat associated siRNA) and modified forms thereof. The above nucleic acid molecule (e.g., siRNA, etc.) may include modified or unmodified RNA, DNA, PNA, or a complex thereof. These RNAi molecules may be commercially available or may be designed and prepared based on known sequence information, etc.

Furthermore, when used herein, the antisense nucleic acid includes modified or unmodified RNA, DNA, PNA, or a complex thereof.

When used herein, the DNA/RNA chimera polynucleotide includes, but is not limited to, a double-strand polynucleotide composed of DNA and RNA that inhibits the expression of a target gene described in for example JP, A, 2003-219893, and a DNA/RNA chimera oligonucleotide described in Park et al., Nucleic Acids Symp Ser. 1999; (42): 225-6.

The drug that suppresses GST-π and the drug that suppresses RB1CC1 may be contained in a single formulation or may be contained separately in two or more formulations. In the case of the latter, each formulation may be administered at the same time or they may be administered with a time interval therebetween. When administered with a time interval therebetween, the formulation containing a drug that suppresses GST-π may be administered prior to the formulation containing a drug that suppresses RB1CC1 or may be administered subsequent thereto.

The present invention also relates to an agent or composition for enhancing the induction of apoptosis and/or the suppression of cell proliferation (hereinafter, also called an "apoptosis-induction enhancing agent", a "cell proliferation-suppression enhancing agent", an "apoptosis-induction enhancing composition" or a "cell proliferation-suppression enhancing composition") by a drug that suppresses GST-π, the agent or composition containing as an active ingredient a drug that suppresses RB1CC1. "Enhancing" the induction of apoptosis and/or the suppression of cell proliferation by means of a drug that suppresses GST-π means increasing the degree of induction of apoptosis and/or suppression of cell proliferation when said enhancing agent is made to act on a cell in addition to a drug that suppresses GST-π compared with the degree of induction of apoptosis and/or suppression of cell proliferation when a drug that suppresses GST-π is utilized.

The degree of increase is not limited and may be for example a degree such that, compared with a time when only a drug that suppresses GST-π is used, the dose of a drug that suppresses GST-π that can give the same effect as when the drug concerned and the enhancing agent are used is decreased by about 1.25 times or greater, about 1.5 times or greater, about 1.75 times or greater, about 2 times or greater, about 2.5 times or greater, about 3 times or greater, about 4 times or greater, about 5 times or greater, about 6 times or greater, about 8 times or greater, about 10 times or greater, about 20 times or greater, about 25 times or greater, about 50 times or greater, or about 100 times or greater (here, for example, the dose being decreased by about 2 times or greater means that the dose is made about ½ or less); in the case of induction of apoptosis, it is a degree such that when the percentage induction of apoptosis when only a drug that suppresses GST-π is utilized is defined as x (%), the percentage induction of apoptosis when the drug that suppresses GST-π and the enhancing agent are utilized (for example, the proportion of cells for which induction of apoptosis is detected relative to the total cells tested) is increased from x by about 5% or greater of (100−x), about 10% or greater, about 15% or greater, about 20% or greater, about 25% or greater, about 30% or greater, about 40% or greater, about 50% or greater, about 60% or greater, about 70% or greater, about 80% or greater, about 90% or greater, about 95% or greater, about 99% or greater, or 100%, and in the case of suppression of cell proliferation, it is a degree such that compared with the number of cells when only a drug that suppresses GST-π is utilized, the number of cells after culturing for a predetermined time after culturing for a predetermined time when the drug that suppresses GST-π and the enhancing agent are utilized is decreased by about 5% or greater, about 10% or greater, about 15% or greater, about 20% or greater, about 25% or greater, about 30% or greater, about 40% or greater, about 50% or greater, about 60% or greater, about 70% or greater, about 80% or greater, about 90% or greater, about 95% or greater, or 100% (here, for example, decreasing the number of cells by about 5% or greater means that when the number of cells after culturing for a predetermined time when only the drug that suppresses GST-π is utilized is y, the number of cells is y−(y×0.05) cells or less).

The amount of active ingredient formulated in the agent or composition of the present invention may be an amount that induces apoptosis and/or suppresses cell proliferation when the agent or composition is administered. Furthermore, it is preferably an amount that does not cause an adverse effect that exceeds the benefit of administration. Such an amount is known or may be determined appropriately by an in vitro test using cultured cells, etc., or a test in a model animal such as a mouse, a rat, a dog, or a pig, and such test methods are well known to a person skilled in the art. Induction of apoptosis may be evaluated by various known techniques, for example, by detection of an apoptosis-specific phenomenon such as DNA fragmentation, binding of annexin V to cell membrane, change in mitochondrial membrane potential, or activation of caspase, or by TUNEL staining. Furthermore, suppression of cell proliferation may be evaluated by various known methods, for example, counting of the number of living cells over time, measurement of the size, volume, or weight of a tumor, measurement of the amount of DNA synthesized, the WST-1 method, the BrdU (bromodeoxyuridine) method, or the $^3$H thymidine incorporation method. The amount of active ingredient formulated can vary according to the manner in which the agent or composition is administered. For example, when a plurality of units of the composition is used for one administration, the amount of active ingredient to be formulated in one unit of the composition may be determined by dividing the amount of active ingredient necessary for one administration by said plurality of units. Adjustment of such a formulation amount can be carried out appropriately by a person skilled in the art.

The present invention also relates to a process for producing an agent or composition for inducing apoptosis or suppressing cell proliferation, the process comprising formulating as active ingredients a drug that suppresses GST-π and a drug that suppresses RB1CC1; use of a drug that suppresses GST-π and a drug that suppresses RB1CC1 in the production of an agent or composition for inducing apoptosis or suppressing cell proliferation; a combination of a drug that suppresses GST-π and a drug that suppresses RB1CC1 for use in the induction of apoptosis or the suppression of cell proliferation; and a method for inducing apoptosis or suppressing cell proliferation, the method comprising administering effective amounts of a drug that suppresses GST-π and a drug that suppresses RB1CC1.

The present invention also relates to a process for producing an agent or composition for inducing apoptosis in a cell in which GST-π is suppressed, the process comprising formulating a drug that suppresses RB1CC1 as an active ingredient; use of a drug that suppresses RB1CC1 in the production of an agent or composition for inducing apoptosis in a cell in which GST-π is suppressed; a drug that suppresses RB1CC1 used in induction of apoptosis in a cell in which GST-π is suppressed; and a method for inducing apoptosis in a cell in which GST-π is suppressed, the method comprising administering an effective amount of a drug that suppresses RB1CC1.

The drug or the formulation amount thereof in the above-mentioned production process or use are as described above. Formulation of each drug may be carried out in accordance with any known technique.

All of the above methods for inducing apoptosis or suppressing cell proliferation may be either an in vitro method or an in vivo method. In the case of an in vivo method, the drug may be administered to a subject that requires it. Furthermore, the drugs in the methods are as described above, and the effective amount of drug may be an amount that induces apoptosis or suppresses cell proliferation in cells to which it is administered. It is also preferably an amount that does not cause an adverse effect that exceeds the benefit of administration. Such an amount is known or may be determined appropriately by an in vitro test using cultured cells, etc., and such a test method is well known to a person skilled in the art. Induction of apoptosis or suppression of cell proliferation may be evaluated by various known techniques, including those described above. The effective amount above need not necessarily be one that effects apoptosis or suppression of cell proliferation in all the cells of a cell population to which the drug is administered. For example, the effective amount above may be an amount that effects apoptosis or suppression of cell proliferation in, of the cell population, at least 1% of the cells, at least 2%, at least 3%, at least 4%, at least 5%, at least 6%, at least 8%, at least 10%, at least 12%, at least 15%, at least 20%, at least 25%, etc.

The apoptosis-inducing and cell proliferation-suppressing agents of the present invention can induce apoptosis or suppression of proliferation effectively even in cells having an abnormality in cell proliferation, etc., and are effective as a component of a pharmaceutical composition. Therefore, one aspect of the present invention includes a pharmaceutical composition containing the apoptosis-inducing agent or the cell proliferation-suppressing agent of the present invention.

The pharmaceutical composition of the present invention is effective in treating a disease in which there is abnormal apoptosis in particular. Therefore, one embodiment of the present invention relates to a pharmaceutical composition for treating a disease in which there is abnormal apoptosis, the pharmaceutical composition containing the apoptosis-inducing agent. When used herein, examples of the disease in which there is abnormal apoptosis include, but are not limited to, a disease due to abnormal cell proliferation, a disease due to KRAS mutation, and a disease due to GST-π overexpression.

Examples of the disease due to abnormal cell proliferation include, but are not limited to, a benign or malignant tumor, hyperplasia, keloid, Cushing's syndrome, primary aldosteronism, erythroplakia, polycythemia vera, leukoplakia, hyperplastic scar, lichen planus, and lentiginosis.

Examples of the disease due to KRAS mutation include, but are not limited to, a benign or malignant tumor (also called a cancer or a malignant neoplasm). Examples of the KRAS mutation include, but are not limited to, a mutation that brings about constitutive activation of KRAS, for example, a mutation that inhibits endogenous GTPase, a mutation that increases the exchange rate of guanine nucleotide, etc. Specific examples of such a mutation include, but are not limited to, a mutation in the $12^{th}$, $13^{th}$, and/or $61^{st}$ amino acid of human KRAS (inhibits endogenous GTPase) and a mutation in the $116^{th}$ and/or $119^{th}$ ammo acid in human KRAS (increases guanine nucleotide exchange rate) (Bos, Cancer Res. 1989; 49 (17): 4682-9, Levi et al., Cancer Res. 1991; 51 (13): 3497-502).

Examples of the diseases due to GST-π overexpression include, but are not limited to, a benign or malignant tumor, in particular a drug-resistant malignant tumor (e.g., resistant to an alkylating agent such as melphalan or cyclophosphamide, an anthracycline-based antitumor antibiotic such as adriamycin, a platinum complex such as cisplatin, etoposide, etc.).

In one embodiment of the present invention, the disease in which there is abnormal apoptosis is a cancer. Examples of the cancer in the present invention include, but are not limited to, sarcomas such as fibrosarcoma, malignant fibrous histiocytoma, liposarcoma, rhabdomyosarcoma, leiomyosarcoma, angiosarcoma, Kaposi's sarcoma, lymphangiosarcoma, synovial sarcoma, chondrosarcoma, and osteosarcoma, carcinomas such as brain tumor, head and neck carcinoma, breast carcinoma, lung carcinoma, esophageal carcinoma, gastric carcinoma, duodenal carcinoma, appendiceal carcinoma, colon carcinoma, rectal carcinoma, liver carcinoma, pancreatic carcinoma, gall bladder carcinoma, bile duct carcinoma, anal carcinoma, renal carcinoma, ureteral carcinoma, bladder carcinoma, prostate carcinoma, penile carcinoma, testicular carcinoma, uterine carcinoma, ovarian carcinoma, vulvar carcinoma, vaginal carcinoma, and skin carcinoma and, furthermore, leukemia and malignant lymphoma. In the present invention, "cancer" includes epithelial malignancy and non-epithelial malignancy. The cancer in the present invention can be present at any site of the body, for example, the brain, head and neck, chest, limbs, lung, heart, thymus, esophagus, stomach, small intestine (duodenum, jejunum, ileum), large intestine (colon, cecum, appendix, rectum), liver, pancreas, gallbladder, anus, kidney, urinary duct, bladder, prostate, penis, testis, uterus, ovary, vulva, vagina, skin, striated muscle, smooth muscle, synovial membrane, cartilage, bone, thyroid, adrenal gland, peritoneum, mesentery, bone marrow, blood, vascular system, lymphatic system such as lymph node, lymphatic fluid, etc.

In one embodiment of the present invention, the cancer includes cancer cells having the mutated KRAS defined above. In one embodiment of the present invention, the cancer includes cancer cells that exhibit hormone- or growth factor-independent proliferation. In one embodiment of the present invention, the cancer includes cancer cells exhibiting GST-π overexpression. In one embodiment of the present invention, the cancer is drug resistant. In one embodiment of the present invention, the cancer has resistance to a medicinal agent selected from the group consisting of an alkylating agent such as melphalan or cyclophosphamide, an anthracycline-based antitumor antibiotic such as adriamycin, a platinum complex such as cisplatin, and etoposide. In one embodiment of the present invention, the cancer has resistance to a medicinal agent selected from the group consisting of melphalan, cyclophosphamide, adriamycin, cisplatin and etoposide.

The present invention also relates to a pharmaceutical composition for treating a disease in which there is abnormal apoptosis, the composition containing as active ingredients a drug that suppresses GST-π and a drug that suppresses RB1CC1; a process for producing a pharmaceutical composition for treating a disease in which there is abnormal apoptosis, the process comprising formulating as active ingredients a drug that suppresses GST-π and a drug that suppresses RB1CC1; use of a drug that suppresses GST-π and a drug that suppresses RB1CC1 for the production of a pharmaceutical composition for treating a disease in which there is abnormal apoptosis; a combination of a drug that suppresses GST-π and a drug that suppresses RB1CC1 for use in the treatment of a disease in which there is abnormal apoptosis; and a method for treating a disease in which there is abnormal apoptosis, the method comprising administering an effective amount of the pharmaceutical composition to a subject that requires same.

The drug, the formulation amount, and the disease in which there is abnormal apoptosis in the above production process or use are as already described. Formulation of each drug may be carried out in accordance with any known technique.

The apoptosis-inducing agent, the cell proliferation inhibitor, and the composition containing same of the present invention may be used in a combination with another active ingredient. Here, being used in combination includes for example administering another active ingredient as a separate formulation, and administering another active ingredient as a mixture with at least one type of other medicinal agent. When administering as a separate formulation, a formulation containing another active ingredient may be administered prior to, at the same time as, or subsequent to another formulation.

Examples of such an active ingredient include one that is effective in treating a disease as a target. For example, when a disease to be treated is a cancer, an anticancer drug may be used in combination. Examples of the anticancer drug include an alkylating agent such as ifosfamide, nimustine hydrochloride, cyclophosphamide, dacarbazine, melphalan, or ranimustine, a metabolism antagonist such as gemcitabine hydrochloride, enocitabine, cytarabine ocfosfate, a cytarabine formulation, a tegafur/uracil or tegafur/gimeracil/oteracil potassium combination drug (e.g., TS-1), doxifluridine, hydroxycarbamide, fluorouracil, methotrexate, or mercaptopurine, an antitumor antibiotic such as idarubicin hydrochloride, epirubicin hydrochloride, daunorubicin hydrochloride, daunorubicin citrate, doxorubicin hydrochloride, pirarubicin hydrochloride, bleomycin hydrochloride, peplomycin sulfate, mitoxantrone hydrochloride, or mitomycin C, an alkaloid such as etoposide, irinotecan hydrochloride, vinorelbine tartarate, docetaxel hydrate, paclitaxel, vincristine sulfate, vindesine sulfate, or vinblastine sulfate, a hormonal therapeutic drug such as anastrozole, tamoxifen citrate, toremifene citrate, bicalutamide, flutamide, or estramustine phosphorate, a platinum complex such as carboplatin, cisplatin (CDDP), or nedaplatin, an angiogenesis inhibitor such as thalidomide, neovastat, or bevacizumab, and L-asparaginase.

Other examples of said other active ingredient include a drug that suppresses autophagy. When used herein, autophagy can include macroautophagy, microautophagy, chaperone-mediated autophagy, etc., but typically means macroautophagy. Therefore, the term "autophagy" in the present invention refers to "macroautophagy" unless otherwise specified.

Autophagy, meaning "self-devouring", is one of the intracellular protein degradation mechanisms, and is in charge of the degradation and recycling of protein within a cell. Autophagy is seen in a wide variety of biological species including yeasts and mammals and is generally accompanied by a series of processes including (a) formation of a PAS (phagophore assembly site), (b) elongation and extension of the phagophore (isolation membrane) surrounding a protein to be degraded and formation of an autophagosome encapsulating the protein to be degraded thereby, (c) formation of an autolysosome by fusion of an autophagosome and a lysosome, and (d) degradation of the protein within the autolysosome.

The above processes (a) to (c) involve specific autophagy-related factors. With regard to the autophagy-related factors, the first research was carried out with yeast, and a large number, including ATG1 to ATG27, have been identified so far (Klionsky et al., Dev Cell. 2003; 5 (4): 539-45); research with mammals has also advanced, a plurality of homologs have been identified, and the core molecular mechanism of autophagy is becoming clear (Yang and Klionsky, Curr Opin Cell Biol. 2010; 22 (2): 124-31).

Examples of autophagy-related factors involved in the core molecular mechanism of autophagy in mammals include those involved in formation of PAS, such as VMP1, TP53INP2, mAtg9, the ULK complex (composed of ULK1, ULK2, mAtg13, and RB1CC1), the PI3K complex (the Atg14L complex composed of Beclin1, hVps34, p150, Ambra1, and Atg14L, and the UVRAG complex composed of Beclin1, hVps34, p150, Bif-1, and UVRAG) and those involved in phagophore elongation such as LC3-II and the Atg12-Atg5-Atg16L complex.

Therefore, examples of the drug that suppresses autophagy include, but are not limited to, a drug that suppresses the production and/or activity of an autophagy-related factor such as those described above and a drug for promoting the degradation and/or inactivation of an autophagy-related factor (when the related factor is a complex, not only the complex itself but individual components forming same are also included). Examples of the drug that suppresses the production of an autophagy-related factor include an RNAi molecule, ribozyme, antisense nucleic acid, or DNA/RNA chimera polynucleotide for DNA encoding an autophagy-related factor, or a vector expressing same.

Examples of the drug that suppresses the activity of an autophagy-related factor include, but are not limited to, a PI3K inhibitor (e.g., wortmannin, etc.), in particular a class III PI3K inhibitor (e.g., 3-MA (3-methyladenine), etc.), a substance that inhibits fusion of an autophagosome and a lysosome (e.g., bafilomycin A1, etc.), a substance that inhibits protein degradation in an autolysosome (e.g., chloroquine, leupeptin, etc.), a substance that binds to an autophagy-related factor (e.g., an antibody for an autophagy-related factor, etc.), and a dominant negative mutant of an autophagy-related factor. These drugs are commercially available or may be produced appropriately based on known techniques.

From the viewpoint of high specificity and low side effects, the drug that suppresses autophagy is preferably an RNAi molecule, ribozyme, antisense nucleic acid, or DNA/RNA chimera polynucleotide for DNA encoding an autophagy-related factor, or a vector expressing same.

Suppression of autophagy may be determined by observing that autophagy is suppressed in cells compared with a case in which the autophagy-suppressing agent of the present invention is not utilized. Suppression of autophagy may be evaluated based on any known technique, examples of which include, but are not limited to, detection of an autophagosome by an electron microscopy method, and detection of an autophagy marker (e.g., Atg5, Atg12, LC3, in particular LC3-II, etc.). LC3-II may be detected by, for example, without being limited to, using a specific antibody for LC3-II, or may be detected by subjecting a sample to separation with electrophoresis, etc., and then detecting LC3-II, separated as a band that is different from LC3-I, by a western blot method, etc., using an antibody that reacts with LC3-II or both LC3-I and LC3-II. Furthermore, because LC3-I is dispersed within the cytoplasm while LC3-II is localized in an autophagy-specific structure such as an isolation membrane, an autophagosome, or an autolysosome, the presence or number of spot-like signals showing these structures, which are manifested by immunostaining, etc., with an antibody that reacts with LC3-II (including an antibody that reacts to both LC3-I and LC3-II) may be used as an indicator for autophagy.

The present invention also relates to an agent or composition for suppressing autophagy in cells in which GST-π is suppressed (also called an "autophagy-suppressing agent" or an "autophagy-suppressing composition"), the agent or composition containing as an active ingredient a drug that suppresses RB1CC1.

In the present invention, suppression of autophagy may be determined by autophagy being suppressed in cells compared with a case in which the agent or composition of the present invention is not utilized. The technique for evaluating autophagy is as described above.

When used herein, "GST-π being suppressed" includes for example a state in which GST-π is being suppressed in cells expressing GST-π. Examples of such a state include a state in which a drug that suppresses GST-π (e.g., those described above, etc.) has been administered to cells expressing GST-π.

Whether or not GST-π is being expressed in certain cells is either known from the literature or may be determined by actually detecting the expression of GST-π in cells. Expression of GST-π may be detected by any known technique, including those described above.

The present invention further relates to a process for producing an agent or composition for suppressing autophagy in cells in which GST-π is suppressed, the process comprising a step of formulating a drug that suppresses RB1CC1; use of a drug that suppresses RB1CC1 in the production of an agent or composition for suppressing autophagy in cells in which GST-π is suppressed; a drug that suppresses RB1CC1 for use in the suppression of autophagy in cells in which GST-π is suppressed; and a method for suppressing autophagy in cells in which GST-π is suppressed, the method comprising administering an effective amount of a drug that suppresses RB1CC1.

The agent or composition for suppressing autophagy of the present invention is useful in the treatment of a state associated with enhanced autophagy under conditions in which GST-π is suppressed. Examples of such a state include, but are not limited to, a state in which expression or activation of GST-π is degraded and a state in which a drug that suppresses expression or activation of GST-π is administered.

Therefore, the present invention also relates to a pharmaceutical composition for treating a state associated with enhanced autophagy under conditions in which GST-π is suppressed, the composition containing as an active ingredient a drug that suppresses RB1CC1; a process for producing a pharmaceutical composition for treating a state associated with enhanced autophagy under conditions in which GST-π is suppressed, the process comprising a step of formulating a drug that suppresses RB1CC1; use of a drug that suppresses RB1CC1 in the production of a pharmaceutical composition for treating a state associated with enhanced autophagy under conditions in which GST-π is suppressed; a drug suppressing RB1CC1 for use in the treatment of a state associated with enhanced autophagy under conditions in which GST-π is suppressed; and a method for treating a state associated with enhanced autophagy under conditions in which GST-π is suppressed, the method comprising administering an effective amount of a drug that suppresses RB1CC1 to a subject requiring same.

The formulation amount of the active ingredient in the agent or composition of the present invention related to the suppression of autophagy may be an amount that achieves suppression of autophagy when the agent or composition is administered. Furthermore, it is preferably an amount that does not cause an adverse effect that exceeds the benefit of administration. Such an amount is known or may be determined appropriately by means of an in vitro test using cultured cells, etc., or a test in a model animal such as a mouse, a rat, a dog, or a pig, and such a test method is well known to a person skilled in the art. Suppression of autophagy may be evaluated by various known techniques, including those described above. The formulation amount of active ingredient can vary according to the mode of administration of the agent or composition. For example, when a plurality of units of the composition is used for one administration, the amount of active ingredient to be formulated in one unit of the composition may be one obtained by dividing the amount of active ingredient necessary for one administration by said plurality of units. Adjustment of such a formulation amount can be carried out appropriately by a person skilled in the art.

The drug and the formulation amount thereof in the production process or use of the agent or composition related to suppression of autophagy are as described above. Formulation of each drug may be carried out in accordance with any known technique.

All of the methods related to suppression of autophagy may be an in vitro method or an in vivo method. Furthermore, the effective amount of drug in the above methods may be an amount that achieves a desired effect (i.e., suppression of autophagy) in cells to which it is administered. Moreover, it is preferably an amount that does not cause an adverse effect that exceeds the benefit of administration. Such an amount is known or may be determined appropriately by an in vitro test, etc., using cultured cells, etc., and such a test method is well known to a person skilled in the art. Achievement of a desired effect may be evaluated by various known techniques, including those described above. The effective amount above need not necessarily be one that induces a desired effect in all the cells of a cell population to which the drug is administered. For example, the effective amount above may be an amount that induces a desired effect in, of the cell population, at least 1% of cells, at least 2%, at least 3%, at least 4%, at least 5%, at least 6%, at least 8%, at least 10%, at least 12%, at least 15%, at least 20%, at least 25%, etc.

When the active ingredient in the various agents or compositions, treatment methods, etc., of the present invention described herein is a nucleic acid, for example, an RNAi molecule, a ribozyme, an antisense nucleic acid, a DNA/RNA chimera polynucleotide, etc., it may be used as a naked nucleic acid as it is, but may also be carried by various vectors. As the vector, any known vector such as a plasmid vector, a phage vector, a phagemid vector, a cosmid vector, or a virus vector may be used. The vector preferably contains at least a promoter that enhances expression of the nucleic acid carried, and in this case the nucleic acid is preferably operably linked to such a promoter. The nucleic acid being operably linked to a promoter referred to herein means that the nucleic acid and the promoter are positioned so that a protein encoded by the nucleic acid is appropriately produced by the action of the promoter. The vector may or may not be replicable in a host cell, and the transcription of a gene may be carried out either outside the nucleus or within the nucleus of a host cell. In the latter case, the nucleic acid may be incorporated into the genome of a host cell.

Furthermore, the active ingredient may be carried by various non-viral lipid or protein carriers. Examples of such carriers include, but are not limited to, cholesterol, a liposome, an antibody protomer, cyclodextrin nanoparticles, a fusion peptide, an aptamer, a biodegradable polylactic acid copolymer, and a polymer; the efficiency of incorporation into cells can be enhanced (see, e.g., Pirollo and Chang, Cancer Res. 2008; 68 (5): 1247-50, etc.). In particular, a cationic liposome or a polymer (e.g., polyethyleneimine, etc.) is useful. Further examples of useful polymers as such a carrier include those described in US 2008/0207553, US 2008/0312174, etc.

With regard to the various pharmaceutical compositions of the present invention described herein, the active ingredient may be combined with another optional component as long as the effect of the active ingredient is not impaired. Examples of such an optional component include another chemical therapeutic agent, a pharmacologically acceptable carrier, an excipient, a diluent, etc. Furthermore, depending on the route of administration, the mode of drug release, etc., the composition may be coated with an appropriate material such as for example an enteric coating or a timed disintegration material, or may be incorporated into an appropriate drug release system.

The various agents and compositions (including the various pharmaceutical compositions) of the present invention described herein may be administered via various routes including both oral and parenteral routes, for example, without limitation, oral, intravenous, intramuscular, subcutaneous, local, intratumoral, rectal, intraarterial, intraportal, intraventricular, transmucosal, transdermal, intranasal, intraperitoneal, intrapulmonary, and intrauterine routes, and may be formulated into a dosage form suitable for each administration route. With regard to such dosage forms and formulation methods, any known form or method may be employed appropriately (see, e.g., Hyojun Yakuzaigaku (Standard Pharmaceutical Science), Ed. by Yoshiteru Watanabe et al., Nankodo, 2003, etc.).

Examples of the dosage form suitable for oral administration include, but are not limited to, a powder, granules, a tablet, a capsule, a liquid, a suspension, an emulsion, a gel, and a syrup, and examples of the dosage form suitable for parenteral administration include an injection such as a solution injection, a suspension injection, an emulsion injection, or an injection in a form that is prepared at the time of use. A formulation for parenteral administration may be in the form of an aqueous or nonaqueous isotonic sterile solution or suspension.

The various agents or compositions (including various pharmaceutical compositions) of the present invention described herein may be targeted at a specific tissue or cells. Targeting may be achieved by any known technique. When delivery to a cancer is attempted, for example, without limitation, a technique such as passive targeting in which a formulation is made into a size of 50 to 200 µm in diameter, in particular 75 to 150 µm, etc., which is suitable for exhibition of an EPR (enhanced permeability and retention) effect, or active targeting in which a ligand of CD19, HER2, a transferrin receptor, a folic acid receptor, a VIP receptor, EGFR (Torchilin, AAPS J. 2007; 9 (2): E128-47), RAAG10 (JP, A (PCT) 2005-532050), PIPA (JP, A (PCT) 2006-506071), or KID3 (JP, A (PCT) 2007-529197), etc., a peptide having an RGD motif or an NGR motif, F3, LyP-1 (Ruoslahti et al., J Cell Biol. 2010; 188 (6): 759-68), etc., is used as a targeting agent may be used. Furthermore, since a retinoid or a derivative thereof is known to be useful as a targeting agent for cancer cells (WO 2008/120815), a carrier containing a retinoid as a targeting agent may also be used. Such carriers are described in the literature above as well as in WO 2009/036368, WO 2010/014117, WO 2012/170952, etc. Various methods for binding a targeting molecule are known (e.g., Torchilin, Nat Rev Drug Discov. 2005; 4 (2): 145-60, Nobs et al., J Pharm Sci. 2004; 93 (8): 1980-92, Marcucci and Lefoulon, Drug Discov Today. 2004; 9 (5): 219-28, etc.), and a person skilled in the art can make various agents or compositions of the present invention (including various types of pharmaceutical compositions) have targeting properties using a targeting molecule based on the above information.

The various agents or compositions (including various pharmaceutical compositions) of the present invention described herein may be supplied in any form, and from the viewpoint of storage stability, may be provided in a form that can be prepared at the time of use, for example, a form that allows a doctor and/or pharmacist, a nurse, another paramedic, etc., to prepare it at the medical site or its vicinity. Such a form is particularly useful when the agent or composition of the present invention contains a component that is difficult to store stably, such as a lipid, a protein, or a nucleic acid. In this case, the agent or composition of the present invention is provided in one or more containers containing at least one of the essential constituents, and preparation is carried out prior to use, for example, within 24 hours, preferably within 3 hours, and more preferably immediately before use. When carrying out preparation, a reagent, a solvent, preparation equipment, etc., that are usually available at a place of preparation may be used as appropriate.

Therefore, the present invention also relates to a kit or pack for preparing a composition, the kit or pack containing one or more containers, the container singly or in combination containing active ingredients to be contained in the various agents or compositions of the present invention; and essential constituents of the various agents or compositions provided in the form of such a kit or pack. The kit or pack of the present invention may include, in addition to the above, instructions such as for example directions for use related to a preparation method, an application method (e.g., an administration method, etc.), etc., for the various agents or compositions of the present invention, for example a written instruction or a recorded medium containing instructions, for example an electronic recording medium such as a flexible disk, a CD, a DVD, a blue-ray disk, a memory card, or a USB memory. Furthermore, the kit or pack of the present invention may contain all of the constituents for completing the various agents or compositions of the present invention, but need not necessarily contain all of the constituents. Therefore, the kit or pack of the present invention need not contain a reagent or a solvent that is usually available at a medical site, an experimental laboratory, etc., such as sterile water, physiological saline, or a glucose solution. The kit or pack of the present invention may be used in the various applications described above relating to the agent or composition of the present invention, for example, induction of apoptosis, suppression of cell proliferation, treatment of a disease in which there is abnormal apoptosis, suppression of autophagy, or treatment of a state associated with enhanced autophagy under conditions in which GST-π is suppressed.

The effective amount in the various treatment methods of the present invention described herein is for example an amount that reduces symptoms of a disease or delays or stops the progress of a disease, and is preferably an amount that suppresses or cures a disease. It is also preferably an amount that does not cause an adverse effect that exceeds the benefit of administration. Such an amount may be determined appropriately by an in vitro test using cultured cells, etc., or a test in a model animal such as a mouse, a rat, a dog, or a pig, and such test methods are well known to a person skilled in the art. Furthermore, the dose of a drug used in the treatment method of the present invention is known to a person skilled in the art or may be determined appropriately by the tests described above, etc.

The specific dose of the active ingredient to be administered in the treatment method of the present invention described herein can be determined by taking into consideration various conditions related to the subject that requires treatment, such as for example the seriousness of symptoms, the general health state of the subject, age, body weight, the gender of the subject, diet, the timing and frequency of administration, concomitant pharmaceuticals, the responsiveness to the treatment, the dosage form and compliance with the treatment.

Examples of the administration route include various routes, including both oral and parenteral routes, such as oral, intravenous, intramuscular, subcutaneous, local, intratumoral, rectal, intraarterial, intraportal, intraventricular, transmucosal, transdermal, intranasal, intraperitoneal, intrapulmonary and intrauterine routes.

The frequency of administration depends on the properties of the agent or composition used and the condition of the subject, including those described above, and may be a plurality of times a day (that is, two, three, four, five, or more times a day), once a day, every few days (that is, every two, three, four, five, six, seven days, etc.), every week, every few weeks (that is, every two, three, four weeks, etc.), etc.

When used herein, the term "subject" means any biological individual and is preferably an animal, more preferably a mammal, and yet more preferably a human individual. In the present invention, the subject may be either healthy or affected by some disease, but when an attempt is made to treat a specific disease, it typically means a subject affected by such a disease or having a risk of being affected.

Furthermore, when used herein, the term "treatment" includes all types of preventive and/or therapeutic interventions medically allowed for the purpose of cure, temporary remission, prevention, etc., of a disease. For example, the term "treatment" includes medically allowable interventions for various types of purposes including delaying or stopping the progress of a disease, making a lesion regress or disappear, preventing onset, or inhibiting recurrence.

EXAMPLES

The present invention is explained in further detail below by reference to Examples, but they are only illustrations and should not be construed as limiting the present invention.

Example 1: Knockdown of GST-π and RB1CC1 by siRNA $1 \times 10^5$ PANC-1 cells (human pancreatic carcinoma-derived) were plated on a 6 cm dish, and culturing was carried out in Roswell Park Memorial Institute 1640 (RPMI 1640, Sigma-Aldrich), to which 10% fetal bovine serum (Fetal bovine serum, FBS) and 5% L-glutamine were added, for 18 hours. Culturing conditions were 37° C. and 5% $CO_2$ unless otherwise specified. Furthermore, $1 \times 10^6$ MIA PaCa-2 cells (human pancreatic carcinoma-derived) and $0.5 \times 10^5$ A549 cells (human lung carcinoma-derived) were plated on a 6 cm dish, and culturing was carried out in Dulbecco's modified Eagle's medium (DMEM, Sigma-Aldrich), to which 10% FBS and 10% L-glutamine were added, for 18 hours. The respective media were replaced with Opti-MEM® (Life Technologies), and 20% to 30% confluent MIA PaCa-2, PANC-1, or A549 cells were transfected with GST-π siRNA and/or RB1CC1 siRNA using Lipofectamine® RNAiMAX (Life Technologies).

A Lipofectamine®/siRNA mixed solution for transfection was prepared as follows. First, 35 µL of Lipofectamine® RNAiMAX and 965 µL of Opti-MEM® were mixed to thus prepare a Lipofectamine® solution. Subsequently, a predetermined amount of 50 µM siRNA was diluted to 1 mL with Opti-MEM® to thus prepare an siRNA solution (for example, when preparing a siRNA solution having a final concentration of 50 nM for use, 6 µL of 50 µM siRNA and 994 µL of Opti-MEM® were mixed), and this was mixed with the Lipofectamine® solution and allowed to stand at room temperature for 15 minutes. As siRNA, those below were used.

```
GST-π siRNA:
                                      (SEQ ID No: 1)
sense chain:    5' GGGAGGCAAGACCUUCAUUtt 3'

(SEQ ID No: 2)
antisense chain: 5' AAUGAAGGUCUUGCCUCCCtg 3'

RB1CC1 siRNA:
                                      (SEQ ID No: 3)
sense chain:    5' GGGACGGAUACAAAUCCAAtt 3'
```

```
                                      (SEQ ID No: 4)
antisense chain: 5' UUGGAUUUGUAUCCGUCCCag 3'

Control siRNA:
                                      (SEQ ID No: 5)
sense chain:    5' ACGUGACACGUUCGGAGAAtt 3'

(SEQ ID No: 6)
antisense chain: 5' UUCUCCGAACGUGUCACGUtt 3'
```

(In the above sequences, uppercase letters indicate RNA and lowercase letters indicate DNA)

In order to test the effect when GST-π siRNA and RB1CC1 siRNA were utilized at the same time, a final concentration of 50 nM of GST-π siRNA or RB1CC1 siRNA or a final concentration of 30 nM of GST-π siRNA and 20 nM of RB1CC1 siRNA when GST-π siRNA and RB1CC1 siRNA were utilized at the same time was added to a dish containing PANC-1, A549, or MIA PaCa-2 cells replaced with 5 mL of Opti-MEM®, culturing was carried out at 37° C. for 5 hours, and the medium was then replaced (5% FBS-containing RPMI 1640 for PANC-1 cells, 10% FBS-containing DMEM for MIA PaCa-2 and A549 cells). After 5 days, the cells were peeled off and harvested from the dish by treatment with trypsin, and the number of cells was counted.

siRNA was not made to act on a non-treated group (No Treatment); after cell plating, culturing was carried out at 37° C. for 6 days, the cells were peeled off and harvested from the dish by treatment with trypsin, and the number of cells was counted. The results are shown in Tables 1 and 2 and FIG. 1. Tables 1 and 2 show the degree of cell proliferation as an increase magnification from the number of plated cells, and FIG. 1 shows the degree of cell proliferation as a relative number when the non-treated group is 100.

TABLE 1

|  | No Treatment | si-GSTP1 50 nM | si-GSTP1 30 nM + si-RB1CC1 20 nM |
| --- | --- | --- | --- |
| MIA PaCa-2 | 47.9 | 1.2 | 0.8 |
| PANC-1 | 21.2 | 1.9 | 1.6 |
| A549 | 114.6 | 20.6 | 10.1 |

TABLE 2

|  | No Treatment | si-RB1CC1 50 nM |
| --- | --- | --- |
| MIA PaCa-2 | 57.6 | 5.6 |
| PANC-1 | 18.0 | 3.4 |
| A549 | 182.8 | 72.4 |

Furthermore, the same experiment as above was carried out for MDA-MB-231 cells (human breast carcinoma-derived) and M7609 cells (human colon carcinoma-derived). $1 \times 10^5$ MDA-MB-231 cells were plated on a 6 cm dish and cultured in 10% FBS- and 10% L-glutamine-containing DMEM for 18 hours, the medium was then replaced with Opti-MEM®, various types of siRNA were utilized for 5 hours, subsequently the medium was replaced with 10% FBS-containing DMEM, after 5 days the cells were harvested, and the number of cells were counted. $1 \times 10^5$ M7609 cells were plated on a 6 cm dish and cultured in 10% FBS- and 5% L-glutamine-containing RPMI 1640 for 18 hours, the medium was then replaced with Opti-MEM®, various types of siRNA were utilized for 5 hours, subsequently the medium was replaced with 10% FBS-containing RPMI 1640, after 5 days the cells were harvested, and the number of cells were counted. The results are shown in FIGS. 2 and 3. FIG. 2 shows the degree of cell proliferation as an increase magnification from the number of plated cells, and FIG. 3 shows the number of cells harvested at the time of completion of the experiment.

From these results, it can be seen that double knockdown of GST-π and RB1CC1 increased the effect in suppressing cell proliferation more than when either one thereof was knocked down.

Example 2: Suppression of Autophagy by Double Knockdown of GST-π and RB1CC1

The effect on autophagy of double knockdown of GST-π and RB1CC1 was investigated. $1 \times 10^6$ MIA PaCa-2 cells were plated on a 6 cm dish, and culturing was carried out in 10% FBS- and 10% L-glutamine-containing DMEM for 24 hours. The medium was replaced with 5 mL of Opti-MEM®, GST-π siRNA, RB1CC1 siRNA, and a mixed solution of GST-π siRNA and RB1CC1 siRNA, prepared in the same way as in Example 1, were added to dishes so that each siRNA had a final concentration of 30 nM, and culturing was carried out at 37° C. for 5 hours; the medium was then replaced by 10% FBS-containing DMEM, and culturing was carried out for 3 days. The cells in the dish were washed with ice-cooled PBS, and an ice-cooled Lysis buffer was then added to thus break the cells. The Lysis buffer was prepared by mixing 100 μL of NP-40 Alternative, PROTEIN GRADE® Detergent, 10% Solution, Sterile-Filtered (Merck Millipore), 500 μL of 1 M Tris-HCl (pH 7.5), 300 μL of 5 M NaCl, 20 μL of 0.5 M EDTA, and 9.08 μL of sterile water. The cell lysate was collected using a cell scraper and ice-cooled for 30 minutes. During this process, inversion mixing was carried out every 10 minutes. The solution thus obtained was subjected to centrifugation at 15000 rpm and 4° C. for 15 minutes, and the supernatant was collected, thus giving a cell extract. This cell extract was subjected to western blot analysis. A reaction with a transfer membrane was carried out at 4° C. for 16 hours using anti-LC3B antibody (Sigma-Aldrich) as a primary antibody. Detection of LC3 molecules was carried out using a chemiluminescent reagent after a reaction with HRP-labeled secondary antibody. Whether or not autophagy was induced was evaluated by a shift to LC3 type I (18 kDa) and type II (16 kDa).

From the results shown in FIG. 4, it can be seen that autophagy was induced by knockdown of GST-π.

$1 \times 10^6$ MIA PaCa-2 cells were plated on a 6 cm dish, and culturing was carried out in 10% FBS- and 10% L-glutamine-containing DMEM for 24 hours. The medium was replaced with 5 mL of Opti-MEM®, GST-π siRNA, RB1CC1 siRNA, and a mixed solution of GST-π siRNA and RB1CC1 siRNA, prepared in the same way as in Example 1, were added to dishes so that each siRNA had a final concentration of 30 nM, and culturing was carried out at 37° C. for 5 hours; the medium was then replaced by 10% FBS-containing DMEM, and culturing was carried out for 3 days. The medium was aspirated from the dish, 1 mL of 4% PFA (Paraformaldehyde)/PBS was added, and the mixture was allowed to stand for 10 to 15 minutes at room temperature. After aspirating the PFA/PBS, 1 mL of 0.5% Triton X-100/PBS was added, and the mixture was allowed to stand for 5 minutes on an ice block. After aspirating the Triton X-100/PBS, 2 mL of PBS was added, and the mixture was allowed to stand for 10 minutes on an ice block. A reaction was carried out using an anti-LC3B antibody (Invitrogen) as a primary antibody at 37° C. for 1 hour. Washing was carried out using PBS, 0.05% Tween® 20/PBS, and PBS in that order for 5 minutes each. A reaction was carried out using Alexa Fluor® 488-labeled anti-rabbit IgG antibody (Life Technologies) as a secondary antibody at 37° C. for 1 hour. Washing was carried out using PBS, 0.05% Tween® 20/PBS, and PBS in that order for 5 minutes each. Mounting was carried out using ProLong® Gold (Life Technologies). After allowing to stand in the dark overnight, Alexa Fluor® 488-derived fluorescence was examined using a fluorescence microscope.

From the results shown in FIGS. 5 to 7, it can be seen that autophagy induced by knockdown of GST-π (strong spot signal in FIG. 6) was substantially completely suppressed by double knockdown of RB1CC1 (FIG. 7). Furthermore, since fragmentation of the nucleus was observed by double knockdown of GST-π and RB1CC1 (shown by arrow in FIG. 7), it can be surmised that suppressing the autophagy that had been induced by knockdown of GST-π by double knockdown of RB1CC1 induced apoptosis.

Example 3: Induction of Apoptosis by Double Knockdown of GST-π and RB1CC1

An examination to see if apoptosis would be induced by double knockdown of GST-π and RB1CC1 was carried out. $1 \times 10^6$ MIA PaCa-2 cells were plated on a 6 cm dish, and culturing was carried out in 10% FBS- and 10% L-glutamine-containing DMEM for 24 hours. The medium was replaced with 5 mL of Opti-MEM®, GST-π siRNA, RB1CC1 siRNA, and a mixed solution of GST-π siRNA and RB1CC1 siRNA, prepared in the same way as in Example 1, were added to dishes so that each siRNA had a final concentration of 30 nM, and culturing was carried out at 37° C. for 5 hours; the medium was then replaced by 10% FBS-containing DMEM, and culturing was carried out for 3 days. The cells of the dish were washed with ice-cooled PBS, and an ice-cooled Lysis buffer was then added to thus break the cells. The Lysis buffer was prepared by mixing 100 μL of NP-40 Alternative, PROTEIN GRADE® Detergent, 10% Solution, Sterile-Filtered, 500 μL of 1 M Tris-HCl (pH 7.5), 300 μL of 5 M NaCl, 20 μL of 0.5 M EDTA, and 9.08 μL of sterile water. The cell lysate was collected using a cell scraper and ice-cooled for 30 minutes. During this process, inversion mixing was carried out every 10 minutes. The solution thus obtained was subjected to centrifugation at 15000 rpm and 4° C. for 15 minutes, and the supernatant was collected, thus giving a cell extract. This cell extract was subjected to western blot analysis. A reaction with a transfer membrane was carried out at 4° C. for 16 hours using anti-Cleaved Caspase-3 antibody (Sigma-Aldrich) as a primary antibody. Detection of Cleaved Caspase-3 molecules was carried out using a chemiluminescent reagent after a reaction with HRP-labeled secondary antibody. Whether or not apoptosis was induced was evaluated by the amount of increase of Cleaved Caspase-3. Since Caspase-3 was cleaved and activated at the time of induction of apoptosis, the presence of cleaved Caspase-3 (Cleaved Caspase-3) can be an indicator for apoptosis.

From the results shown in FIG. 8, it can be seen that apoptosis was induced by double knockdown of GST-π and RB1CC1. From the results of FIGS. 4 to 8, it can be seen that apoptosis was induced by suppressing autophagy, induced by knockdown of GST-π, by double knockdown of RB1CC1.

The invention claimed is:

1. A method for treating autophagy induced by the inhibition of glutathione S-transferase π (GST-π) expression, the method comprising administering an effective amount of a pharmaceutical composition to a subject in need thereof, the composition comprising as an active ingredient a drug that suppresses RB1-inducible coiled-coil protein 1 (RB1CC1).

2. The method according to claim 1, wherein the active ingredient is selected from the group consisting of an RNAi molecule, a ribozyme, an antisense nucleic acid, a DNA/RNA chimera polynucleotide and a vector expressing same.

* * * * *

UNITED STATES PATENT AND TRADEMARK OFFICE
CERTIFICATE OF CORRECTION

Page 1 of 1

PATENT NO. : 10,093,931 B2
APPLICATION NO. : 15/319582
DATED : October 9, 2018
INVENTOR(S) : Yoshiro Niitsu It is certified that error appears in the above-identified patent and that said Letters Patent is hereby corrected as shown below:

In the Specification

In Column 3, Line 46, change "RB" to --RB1CC1--

In Column 4, Line 44, change "RB" to --RB1CC1--

In Column 5, Line 4, change "Piloprost" to --piriprost--

In Column 6, Line 4, change "RB" to --RB1CC1--

In Column 9, Line 33, change "ammo" to --amino--

In Column 11, Line 8, change "tartarate," to --tartrate,--

Signed and Sealed this
Nineteenth Day of February, 2019

Andrei Iancu
*Director of the United States Patent and Trademark Office*